United States Patent [19]
Karami

[11] 3,994,299
[45] *Nov. 30, 1976

[54] ABSORBENT ARTICLE

[75] Inventor: Hamzeh Karami, Crystal Lake, Ill.

[73] Assignee: Colgate-Palmolive Company, New York, N.Y.

[ * ] Notice: The portion of the term of this patent subsequent to June 29, 1993, has been disclaimed.

[22] Filed: Feb. 24, 1975

[21] Appl. No.: 552,463

[52] U.S. Cl. .............................. 128/287; 128/284; 128/290 R
[51] Int. Cl.² ......................................... A61F 13/16
[58] Field of Search ............... 128/284, 287, 290 R, 128/296, 290 W; 156/201; 428/198, 195

[56] References Cited
UNITED STATES PATENTS

| | | |
|---|---|---|
| 2,862,251 | 12/1958 | Kalwaites ...................... 128/290 W |
| 3,221,738 | 12/1965 | Ekberg et al. ....................... 128/287 |
| 3,344,789 | 10/1967 | Arnold et al. ......................... 128/287 |
| 3,559,648 | 2/1971 | Mason, Jr. ........................... 128/287 |
| 3,620,894 | 11/1971 | Oates ............................ 128/296 X |
| 3,665,921 | 5/1972 | Stumpf ................................ 128/287 |
| 3,814,101 | 6/1974 | Kozak .................................. 128/287 |
| 3,842,838 | 10/1974 | Gellert ................................ 128/284 |
| 3,868,287 | 2/1975 | Lewyckyj ............................. 156/201 |
| 3,875,942 | 4/1975 | Roberts ............................... 128/287 |
| 3,881,489 | 5/1975 | Hartwell .............................. 128/287 |
| 3,886,941 | 6/1975 | Duane ................................. 128/287 |
| 3,903,890 | 9/1975 | Mesek ................................. 128/287 |
| 3,927,673 | 12/1975 | Taylor ................................. 128/287 |
| 3,945,386 | 3/1976 | Anczurowski ...................... 128/287 |
| 3,965,906 | 6/1976 | Karami ............................... 128/287 |

Primary Examiner—Aldrich F. Medbery
Attorney, Agent, or Firm—Powell L. Sprunger

[57] ABSTRACT

An absorbent article comprising an absorbent pad having a front surface, a fluid pervious top sheet covering at least a portion of the front surface of the pad, and a perforated film of thermoplastic material intermediate the sheet and pad. The film is heated to enlarge the perforations and fuse the film to the sheet and pad.

13 Claims, 6 Drawing Figures

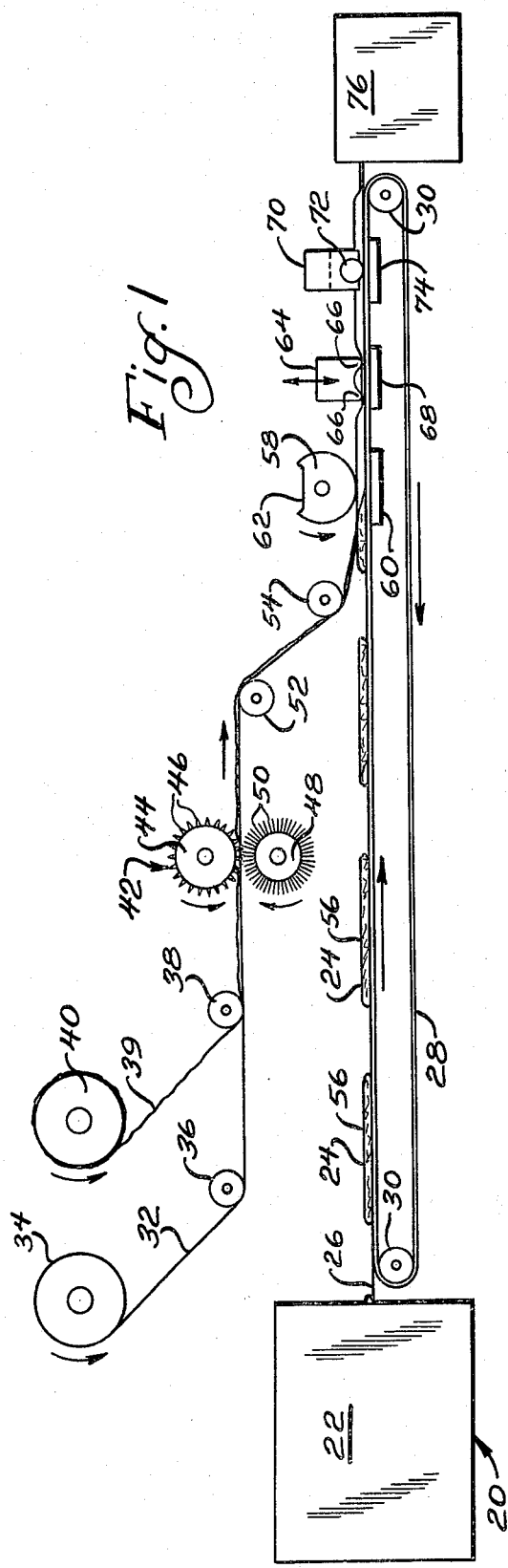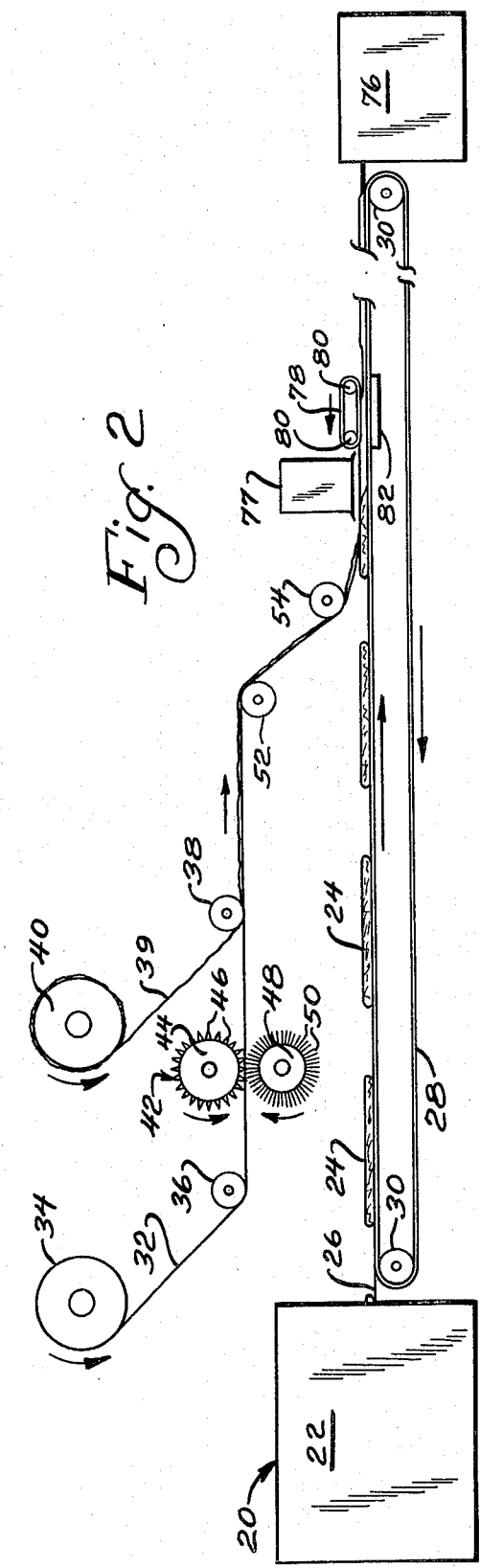

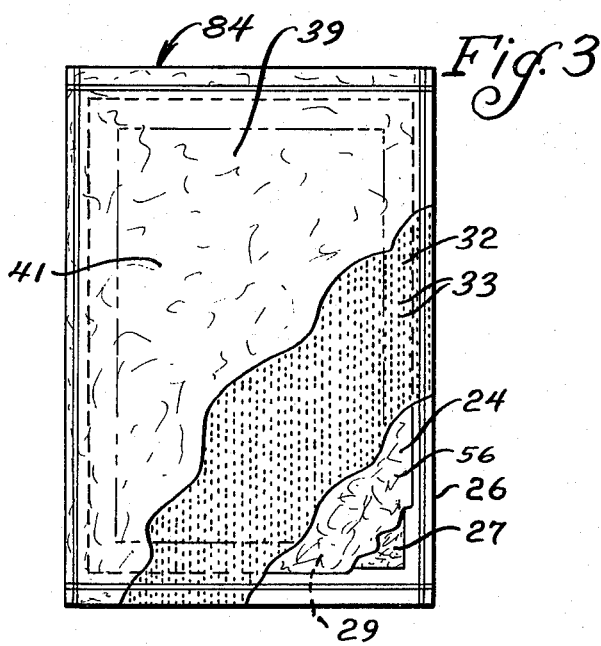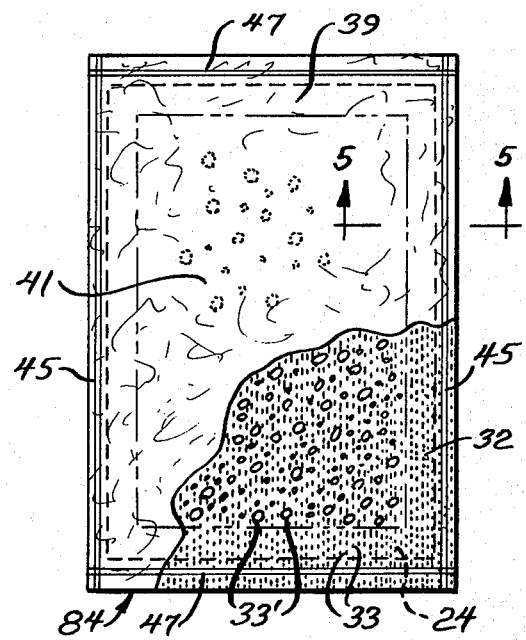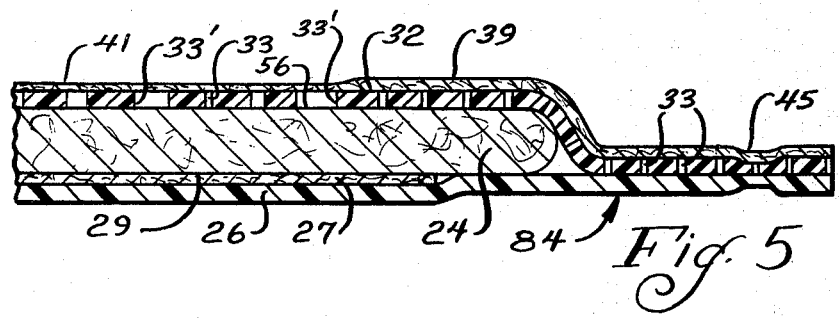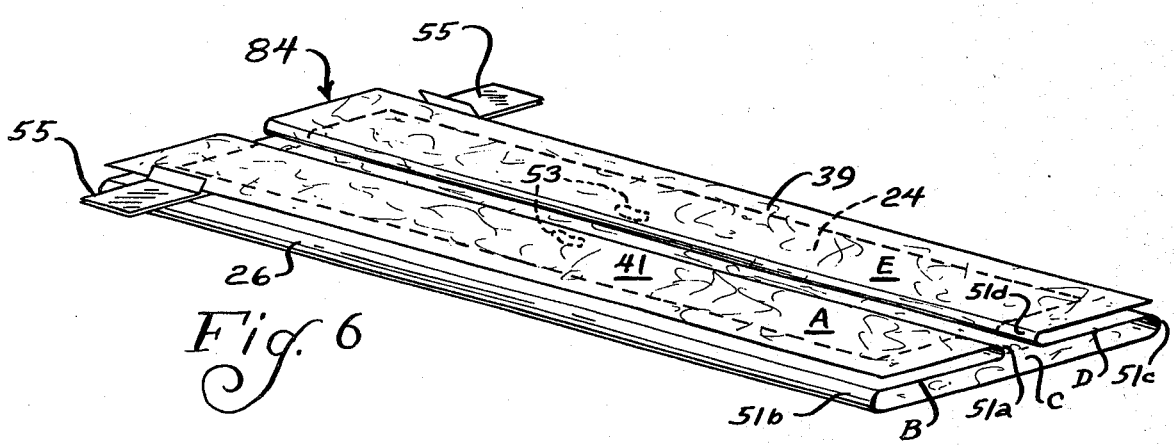

ABSORBENT ARTICLE

BACKGROUND OF THE INVENTION

The present invention relates to absorbent articles.

A various assortment of absorbent articles of the disposable type, such as diapers and sanitary pads, have been proposed which are discarded after a single use. Several factors are of importance in determining whether such articles will be acceptable to the consumer. The articles should rapidly receive and dissipate body fluids without a significant amount of backwetting to the wearer's skin and without wicking and leakage from the article, while providing comfort to the wearer. Such absorbent articles also should be available to the consumer at a relatively low cost, since they are not reused.

Much of the cost and deficiencies in prior articles may be attributed to the structure of and the materials used in the articles. In the case of disposable diapers, structures are often provided having an absorbent pad, a fluid impervious backing sheet covering a back surface of the pad, and a fluid pervious top sheet covering a front surface of the pad. Particularly in the case where the absorbent pads are made of a mass of fibers, such as comminuted wood pulp, an absorbent wadding sheet is often placed over the front surface of the pad to maintain structural integrity of the pad when wet. In addition to adding to the cost of the diapers, such top wadding sheets impair the function of the diaper in a number of respects. The wadding sheets impede the rapidity of fluid passage from the top sheet into the pad, and retain fluid adjacent the front surface of the diaper, thus increasing the amount of backwetting from the diaper to the infant. The wadding sheet also adds stiffness to the diaper, thus decreasing the amount of comfort the diaper provides for the infant.

In the past, the top sheet of the diaper, which is usually made of nonwoven material, has been made relatively thick and strong to prevent breaking up of the top sheet when it becomes wet during use. The relatively heavy top sheet utilized in prior diapers also adds significantly to the cost of the diaper.

SUMMARY OF THE INVENTION

A principal feature of the present invention is the provision of an absorbent article of simplified construction and reduced cost.

The article of the present invention comprises, an absorbent pad having a front and back surface, a fluid pervious top sheet covering the front surface of the pad, a fluid impervious backing sheet covering the back surface of the pad, and a perforated thermoplastic film intermediate the top sheet and pad. The film is heated to enlarge the perforations and fuse the film to the top sheet and pad.

A feature of the invention is that the enlarged perforations permit passage of fluid through the top sheet and film to the pad.

Another feature of the invention is that the film prevents backwetting of fluid from the pad to the top sheet.

Still another feature of the invention is that the fused film maintains the structural integrity of the pad and eliminates the necessity for a top wadding sheet for the pad.

Yet another feature of the invention is that the article permits rapid passage of fluid from the top sheet to the pad due to elimination of the top wadding sheet.

Another feature of the invention is that the article reduces backwetting from the pad due to elimination of the top wadding sheet.

A further feature of the invention is that the article is more pliable and has a better hand due to elimination of the top wadding sheet.

Thus, another feature of the invention is that the article of the present invention is more comfortable to the skin of a user.

A further feature of the invention is that the fused film reinforces the top sheet and permits the use of a relatively thin material for the top sheet without breaking up during use.

Thus, a feature of the invention is that elimination of the top wadding sheet and the reduction in thickness of the top sheet reduces the cost of the absorbent article.

In a preferred embodiment of the article of the present invention the top and backing sheets and film extend past side and end edges of the pad, and the sheets and film are fused together along the side and end edges of the pad.

Thus, another feature of the present invention is that the film and top and backing sheets are joined together in a simplified manner.

Yet another feature of the invention is that the enlarged perforations are preferably spaced from the edges of the pad and are located over the pad, such that the film and backing sheet provide a fluid barrier adjacent the edges of the pad to prevent wicking and leakage from the pad.

Still another feature of the invention is the provision of a method for making the absorbent article of the present invention.

Further features will become more fully apparent in the following description of the embodiments of this invention and from the appended claims.

DESCRIPTION OF THE DRAWINGS

In the drawings:

FIG. 1 is a diagrammatic view illustrating an apparatus for making an absorbent article according to a method of the present invention;

FIG. 2 is a diagrammatic view illustrating another apparatus for making an absorbent article according to a method of the present invention;

FIG. 3 is a front plan view partly broken away, illustrating a partially constructed absorbent article or diaper of the present invention;

FIG. 4 is a front plan view, partly broken away, of a disposable diaper of the present invention;

FIG. 5 is a fragmentary sectional view taken substantially as indicated along the line 5—5 of FIG. 4; and FIG. 6 is a perspective view of the diaper of FIG. 4 folded into a box-pleat configuration.

DESCRIPTION OF THE PREFERRED ENBOMIMENTS

Although, for convenience, the absorbent article of the present invention will be described as a disposable diaper, it will be understood that the description is applicable to other suitable absorbent articles. For example, other illustrative articles which may be constructed according to the present invention are sanitary pads, maternity napkins, and wound dressings.

Referring now to FIG. 1, there is shown an apparatus, generally designated 20, for making an absorbent article, such as a disposable diaper, according to a method of the present invention. The apparatus 20 has a first section 22 which cuts an absorbent material, such as comminuted wood pulp, into lengths as absorbent pads 24, and places the pads 24 in a spaced relationship on a fluid impervious backing sheet 26, such as polyethylene, as the backing sheet passes onto an endless belt 28. The belt 28 is supported and driven by a pair of rollers 30, with the belt 28 being driven in a direction such that the backing sheet 26 and pads 24 are carried from the first section 22, as indicated by the direction of the arrows in the drawings.

A web of thermoplastic material 32, such as a film of polyethylene, is unwound from a roll 34 and passes beneath a roller 36 to a roller 38 where it joins a web 39 of fluid pervious material, such as a nonwoven material, which is unwound from a roll 40. The webs 32 and 39 pass from the roller 38 to a perforator generally designated 42.

The perforator 42 has an upper roll 44 having a plurality of closely spaced needles or pins 46 projecting outwardly from the roll 44 peripherally around the roll. The perforator 42 also has a lower roll 48 defining a resilient substrate for the upper roll 44 to maintain the webs 32 and 39 against the upper roll and receive the points of the needles 46 as they pass through the webs. The lower roll 48 may have a plurality of metal bristles 50 projecting outwardly from the roll and extending peripherally around the roll, thus defining a brushlike surface for the roll. In another embodiment, the lower roll 48 may have a soft surface, such as rubber, to receive the points of the needles. Thus, as the webs 32 and 39 pass between the upper and lower rolls 44 and 48 of the perforator 42, the needles 46 of the upper roll 44 pass through the webs 32 and 39 and perforate the thermoplastic film or web 32 with perforations, as further described below. The needles 46 of the upper roll 44 may extend throughout a sufficient width of the roll 44, if desired, to perforate the entire width of the web 32, or the needles may be spaced from side edges of the web 32, for a purpose which will be described below.

The perforated webs 32 and 39 then pass over roller 52 and under roller 54 to a location over the pads 24 on the belt 28 where the webs are placed over the front surface 56 of the pads, as shown. A heated roll 58, which preferably has a relatively smooth outer surface, contacts the web 39 of fluid pervious material as the webs 32 and 39 and pads 24 pass beneath the roll 58, and heats the web 32 of thermoplastic material through the web 39. A supporting member 60 is provided beneath the belt 28, such that the pads 24 and webs may be slightly compressed between the roll 58 and supporting member 60 as the web 32 is heated. The heat applied to the web 32 of thermoplastic material causes the perforations in the web to enlarge from the configuration as initially perforated, and the heated web 32 is also fused against the compressed web 39 and pad 24, as will be further described below. THe heated roll 58 has a cutout portion 62 to prevent contact of the roll 58 against the webs 32 and 39 intermediate the pads 24 as they pass beneath the roll.

A heated member 64, which is mounted for reciprocal vertical movement, has a pair of laterally extending ribs 66 which contact and heat the webs 32 and 39 and the backing sheet 26 along lateral lines intermediate the pads 24, and thus fuse the webs 32 and 39 and backing sheet 26 together adjacent end edges of the pads 24. A supporting member 68 is provided beneath the belt 28 to facilitate operation of the heated member 64 in fusing the webs and backing sheet together. The heated member 64 is spaced away from the webs 32 and 39 when the pads 24 pass beneath the member 64, and is brought into lower sealing position intermediate end edges of the pads.

Preferably, the webs 32 and 39 and backing sheet 26 have a greater width than the pads 24, such that the webs and sheet extend past side edges of the pads. As the pads pass along the belt 28, the webs and backing sheet covering the pads 24 pass beneath a second heated member 70 having a pair of spaced heated rollers 72 located adjacent the opposed side edges of the pads 24. The heated rollers 72 contact the web 39 and continuously fuse the webs 32 and 39 and backing sheet 26 together along side edges of the pads 24, such that the heat seal lines extend the length of the pads and cross the lateral heat seal lines made by the first heated member 64. A supporting member 74 provides a support surface for operation of the heated rollers 72 in fusing the webs and backing sheet together. The pads 24 then pass from the belt 28 to a second section 76, where the pads are severed from each other intermediate the lateral heat seal lines formed by the heated member 64, and the separated pads are folded and packaged, as desired.

Another apparatus 20 for making absorbent articles according to the present invention is illustrated in FIG. 2, in which like reference numerals designate like parts. In this embodiment, the perforator 42 perforates the web 32 of thermoplastic material prior to being placed against the web 39 adjacent the roller 38. As the webs 32 and 39 are placed on the pads 24, a blower 77 blows hot air against the web 39 to heat the web 32 and enlarge the perforations in the web 32. Prior to cooling of the web 32, the pad structure is passed beneath a belt 78 which is supported and driven by a pair of rollers 80. The belt 78 compresses the webs 32 and 39 and pads 24 between the belt 28 and support member 82 to fuse the still heated web 32 to the web 39 and pad 24. The heated members 64 and 70, which are described in connection with the device of FIG. 1, may be utilized to fuse the webs 32 and 39 and backing sheet 26 together adjacent side and end edges of the pads 24, if desired.

It will be understood that many other variations are within the scope of the present invention. For example, the perforated web 32 of thermoplastic material may be heated to enlarge the perforations prior to placement of the web 32 against the web 39 of fluid pervious material. If desired, the web 32 of thermoplastic material may be fused to the web 39 prior to perforating the webs 32 and 39, and the fused webs 32 and 39 may be subsequently heated to enlarge the perforations. It is contemplated that enlarged openings may be punched through the web 32, after which the web 32 may be laminated or fused to the web 39 and pads. If desired, the needles 46 may be spaced from the side edges of the web 32, such that the perforations only overlie the pads or are laterally confined to the areas of the web 32 which are fused to the pads. Also, the needles 46 may be spaced in peripheral portions of the perforator 42, in order that the longitudinal sections of the web 32 intermediate the end edges of the pads are not perforated.

A disposable diaper generally designated 84 which is made according to the present invention is illustrated in FIGS. 3–6. As shown in FIG. 3, the diaper 84 as partially formed has an absorbent pad 24, such as comminuted wood pulp forming a mass of fibers, a fluid impervious backing sheet 26 preferably of a thermoplastic material, such as polyethylene, covering a back surface 29 of the absorbent pad 24, a sheet of cellulose wadding 27 intermediate the backing sheet 26 and pad 24, a film 32 of thermoplastic material, such as polyethylene, having a plurality of small perforations 33, with the film 32 covering a front surface 56 of the pad 24, and a fluid pervious top or cover sheet 39, such as a nonwoven material, covering the film 32. The diaper 84 or pad assembly has a fluid receiving region 41 generally in the longitudinal and lateral central region of the diaper. The perforations 33 in the diaper of FIG. 3 are shown prior to heating, and are shown as extending the width and length of the film 32.

As illustrated in FIGS. 4 and 5, after the film 32 is heated, a large number of perforations 33 in the film 32 are enlarged to openings 33' which permit passage of fluid through the film 32. As previously discussed, the heated film 32 is also fused or laminated to the top sheet 39 and the underlying pad 24. The heated film becomes anchored to fibers in the pad and top sheet, which is facilitated by compression of the diaper while the film is hot. The film which is fused to the pad maintains structural integrity of the pad 24 when wet, and eliminates the necessity for placing a sheet of absorbent wadding over the front surface 56 of the pad, which would otherwise be required to prevent breaking up and balling of the pad.

During use of the diaper fluid passes through the top sheet 39 and the enlarged openings 33' directly into the pad 24. Elimination of the top wadding sheet increases the rapidity with which fluid passes into the pad, since the top wadding sheet normally impedes the passage of fluid into the pad. Additionally, backwetting from the pad to the top sheet is reduced by elimination of the top wadding sheet, since the wadding sheet would normally retain fluid adjacent the top sheet after being wetted. Backwetting from the absorbent pad is also prevented by the film 32 which provides a fluid impervious barrier throughout a substantial area of the diaper. Elimination of the top wadding sheet also permits greater conformability of the diaper, since the top wadding sheet normally causes some stiffness to the front of the diaper, and the diaper of the present invention thus has a better hand and provides a more comfortable surface for the infant's skin. In addition, elimination of the top wadding sheet reduces the cost of materials in the diaper.

Relatively thick nonwoven materials have been utilized in the past for top sheets in diapers to prevent breaking up of the top sheets when wetted or moved during use. However, the thermoplastic film 32, which is fused to the top sheet 39, reinforces the top sheet and permits the use of a relatively thin material for the top sheet in the diaper of the present invention. A normal weight for the nonwoven materials utilized in conventional diapers is approximately 18-22 grams/square yard, whereas a relatively thin top sheet of nonwoven material having a weight of 7-14 grams/square yard may be readily used in the diaper of the present invention without breaking up or tearing of the top sheet during use of the diaper, thus significantly reducing the cost of materials for the diaper. The passage of fibers from the pad through the relatively thin top sheet is prevented by the film 32.

As shown in FIGS. 4 and 5, the top sheet 39, film 32, and backing sheet 26 extend past side and end edges of the pad 24, and the sheets and film are fused on lines 45 along side edges of the pad and lines 47 along end edges of the pad. As shown, the film 32 may be heated only in the central region 41 of the diaper, such that the enlarged openings 33' are spaced from the side and end edges of the pad. Thus, the fluid impervious film 32 and backing sheet 26 provide a fluid barrier adjacent side and end edges of the pad to prevent wicking and leakage from the edges of the pad during use of the diaper. If the perforations 33 extend to the side and end edges of the film 32, the small perforations 33 permit little or no leakage through the film 32. Alternatively, the perforations 33 may be spaced from the side edges of the film 32, as well as the end edges of the film, if desired.

In a preferred embodiment of the diaper of the present invention, the thermoplastic film 32 may have a thickness of 0.2 to 0.5 mils, and the top sheet may have a weight of 10-14 grams/square yard. In a satisfactory structure, the largest distance across the perforations or openings 33 may be in the range of 0.2 to 7 mms prior to heating the film 32, whereas the largest distance across the enlarge openings 33' may be in the range of 0.2 to 8 mms. It is noted in this regard that some of the perforations 33 may not be enlarged when the film 32 is heated. The film 32, if polyethylene, may be heated at approximately 250° to 300° F. to enlarge the perforations and fuse the film to the top sheet and pad. The size of the openings 33' may be determined in part by the initial size of the perforations 33 and the extent to which the film 32 is heated after being perforated, both in temperature and length of time. It will be understood that the words "perforations" and "perforating", and other words of similar effect, are used herein for convenience, and should not be considered as limiting the present invention. Thus, it is intended that "perforations" may comprise holes, apertures, slits, or other openings of regular or irregular shape. Also, it is contemplated that "perforating" comprises an operation or operations which provide such perforations. The enlarged openings 33' may also have a regular or irregular shape.

As illustrated in FIG. 6, the diaper 84 may be folded into a box-pleat configuration along a plurality of longitudinally extending fold lines 51a, 51b, 51c, and 51d defining a longitudinally extending central panel C, a pair of first panels B and D extending from and overlying the front surface of the central panel C, and a pair of outermost panels A and E extending from and overlying the first panels B and D. The pleats in the panels may be retained to the front surface of the central panel C by a pair of adhesive spots 53. The diaper 84 may have a pair of conventional tape fasteners 55 for securing the diaper about an infant during placement. In other respects, the diaper may conform to the structure of the diaper described in connection with FIGS. 4 and 5.

The foregoing detailed description is given for clearness of understanding only, and no unnecessary limitations should be understood therefrom, as modifications will be obvious to those skilled in the art.

I claim:
1. An absorbent article, comprising: an absorbent pad having a front surface, and a fluid pervious, fibrous cover sheet fused to the front surface of the pad throughout a substantial portion of a longitudinally extending central fluid receiving region of the pad, said cover sheet being fused to the pad by a heated film of thermoplastic material intermediate the cover sheet and pad, with said film having a plurality of openings in the fluid receiving region of the pad communicating between the cover sheet and the pad, with said openings comprising perforations in the film enlarged by heating.

2. The article of claim 1 wherein the absorbent pad comprises a mass of fibers and the cover sheet is fused to fibers in the pad.

3. An absorbent article comprising, an absorbent pad having a front surface, a fluid pervious top sheet covering at least a portion of the front surface of the pad, and a film of thermoplastic material intermediate the top sheet and pad, said film being fused in a region of said film over said pad, said film having a plurality of openings extending through the film in a fluid receiving area of the article, and wherein said film is fused to both said top sheet and pad in said region.

4. The article of claim 3 wherein said openings comprise perforations in the film enlarged by heating.

5. An absorbent article, comprising: an absorbent pad assembly including an absorbent pad having a front surface, a back surface, a pair of side edges, and a pair of end edges, the pad assembly having a fluid pervious top sheet covering at least a substantial portion of the front surface of said pad, a film of thermoplastic material intermediate and fused to the top sheet and pad in a region overlying the pad, said film having a plurality of perforations extending through the film, at least a part of said perforations being enlarged by heating in a fluid receiving area of the pad assembly in said region, and a fluid impervious backing sheet covering at least a substantial portion of the back surface of the pad.

6. The article of claim 5 wherein the enlarged perforations are spaced from side edges of the film.

7. The article of claim 5 wherein the enlarged perforations are spaced from end edges of the film.

8. The article of claim 6 wherein the enlarged perforations are spaced from end edges of the film, the film extends past the side and end edges of the pad, and the enlarged perforations are spaced from the side and end edges of the pad.

9. The article of claim 5 wherein the perforations extend substantially throughout the width and length of said film.

10. The article of claim 5 wherein the marginal edges of the top sheet, film and backing sheet extend past the side and end edges of the pad, and the marginal edges of the sheets and film are fused together along the side and end edges of the pad.

11. The article of claim 5 wherein the pad assembly comprises a disposable diaper, and the enlarged perforations are located in at least a crotch region of the diaper.

12. The article of claim 5 wherein the top sheet comprises a nonwoven material having a weight approximately in the range of 7 to 14 grams/square yard.

13. The article of claim 5 wherein said film has a thickness of approximately 0.2 to 0.5 mils.

* * * * *